United States Patent
Grant

(10) Patent No.: US 6,676,409 B2
(45) Date of Patent: Jan. 13, 2004

(54) DENTAL TOOL

(75) Inventor: Sidney Grant, London (GB)

(73) Assignee: Medivance Instruments Limited (GB)

( * ) Notice: Subject to any disclaimer, the term of this patent is extended or adjusted under 35 U.S.C. 154(b) by 204 days.

(21) Appl. No.: 09/990,020

(22) Filed: Nov. 21, 2001

(65) Prior Publication Data

US 2003/0027100 A1 Feb. 6, 2003

(30) Foreign Application Priority Data

Aug. 1, 2001 (GB) .............................................. 0118778
Oct. 31, 2001 (GB) .............................................. 0126177

(51) Int. Cl.⁷ ................................................ A61C 3/02
(52) U.S. Cl. ...................................................... 433/88
(58) Field of Search ........................ 433/88, 89; 451/90, 451/102

(56) References Cited

U.S. PATENT DOCUMENTS

| 4,412,402 A | 11/1983 | Gallant |
| 4,462,803 A | 7/1984 | Landgraf et al. |
| 4,492,575 A | 1/1985 | Mabille |
| 4,676,749 A | 6/1987 | Mabille |
| 4,771,580 A * | 9/1988 | Male |
| 4,995,202 A * | 2/1991 | Gardner et al. |
| 5,120,219 A * | 6/1992 | De Farcy ..................... 433/88 |

FOREIGN PATENT DOCUMENTS

| CH | 656524 | 7/1986 |
| EP | 0097288 | 1/1984 |
| EP | 0948941 A2 | 10/1999 |
| EP | 1145689 | 10/2001 |
| GB | 2026359 | 2/1980 |
| JP | 2001204741 | 7/2001 |
| WO | WO 01/21087 A1 | 3/2001 |

OTHER PUBLICATIONS

Patents Act 1977: Search Report under Section 17 dated Jan. 28, 2003.
International Search Report based on British Application No. 0118778.0.

* cited by examiner

*Primary Examiner*—Cary E. O'Connor
(74) *Attorney, Agent, or Firm*—Caesar, Rivise, Bernstein, Cohen & Pokotilow, Ltd.

(57) ABSTRACT

A dental tool for the delivery of pressurized air containing abrasive media includes a supply of unpressurized water which joins the leading end of the tool at a location at which the water is drawn to form a curtain about the pressurized air/media flow.

10 Claims, 4 Drawing Sheets

DENTAL TOOL

The present invention relates to a tool for use in dentistry.

Air abrasive cutting is currently in regular use in dental practice and is an extremely useful technique in modern adhesive dentistry where resurfacing and filling materials adhere to the tooth rather than the material, such as amalgams that are keyed for retention. This means that decay can be removed by a process, such as air abrasion, which will remove the decay without the need to cut sound tooth material in order to achieve retention. The surface prepared with the gas abrasive technique leaves a surface ideal for the new materials to bond to. Another advantage of the gas abrasive technique is low stress cutting of the tooth avoiding the stress fracturing found when using conventional rotary instruments. The system also benefits from almost zero heat generation in the cutting process and reduces the need for injections. However the process is slow unless high pressure in the gas or lower pressure and high levels of abrasive media are used. High pressure up to ten bar in some instruments means that the instruments can be difficult to control when cutting teeth, which by nature vary from patient to patient in hardness. There is a relationship between the pain factor and the pressure factor. The higher the pressure, the greater the sensitivity. Increasing the rate of abrasive to air to maintain high cutting rate means that one has a higher than desirable dust debris problem requiring very effective recovery equipment, like powerful aspirators and even external evacuation for airborne particles escaping the oral cavity. Many attachments have been developed in an attempt to eliminate this drawback of gas abrasion devices. These take the form of flexible plastic membrane mouldings that encompass the tip and create a containment area against the tooth surface. These are often connected to aspiration tubes in an attempt to remove the cutting media from the mouth and the cutting face. The problem with these devices is that they encompass the area being cut or polished and observation for the operator is through the device or by lifting away for inspection of the area under treatment. These devices become quickly obscured by the very nature of the materials they are controlling. The invention is based on the realisation that the problem of dust control may be achieved by surrounding the gas stream with a curtain of liquid, conveniently water. Further, the invention is based on the realisation that by forming the curtain in a defined way many benefits result.

In one aspect the invention provides a dental tool comprising a body having a nozzle for providing a stream of pressurised gas containing abrasive media towards a tooth surface, a cap member extending forwardly of the outlet end of the nozzle, the cap member having a bore in generally axial alignment with the bore of the nozzle, the cap having a liquid supply pipe opening into the bore rearwardly of the nozzle outlet, the wall of the bore forwardly of the nozzle being shaped so that liquid emerging from the outlet is caused by the gas stream to form a wall of liquid about the gas stream moving towards the tooth surface.

In another aspect the invention provides a method of treating a tooth, the method comprising drawing a stream of pressurised gas towards the tooth surface, the gas containing abrasive media, the method including the step of drawing a liquid to join the gas stream and shaping the liquid to form a wall about the gas stream.

In yet another aspect there is provided a dental tool comprising a tube having a tapered leading end forming a nozzle of a predetermined diameter, the tube being arranged to supply pressurised gas containing abrasive media to the nozzle, and a cap therefor, the cap having a body of substantially the same shape and a nozzle having a diameter of substantially the same order, a liquid supply tube connected to the cap and having an outlet at a location rearward of the nozzle.

In the invention the liquid is unpressurised and is drawn by the flow of pressurised gas to form a wall about the gas stream. That wall acts as a shielding curtain and has several beneficial effects, as explained in better detail below. While we do not wish the monopoly to be restricted in any way by the following theory, our investigations suggest that the unpressurised drawn liquid is subjected to a Venturi effect to form the curtain.

In yet another aspect the invention provides a dental tool comprising a body having means at one end for performing a dental treatment, and a liquid supply pipeline arranged to supply liquid to the one end, wherein a hand controlled pinch valve is mounted on the tool to control the supply of liquid to the one end.

In yet another aspect the invention provides a dental tool comprising a body having means at one end for performing a dental treatment, the means being at the end of an extension of the body, the extension being rotatable relative to the body.

Other features of the invention are set out in the subclaims.

One embodiment of the dental tool will now be described by way of example only with reference to the accompanying diagrammatic drawings, wherein.

Figure 1:
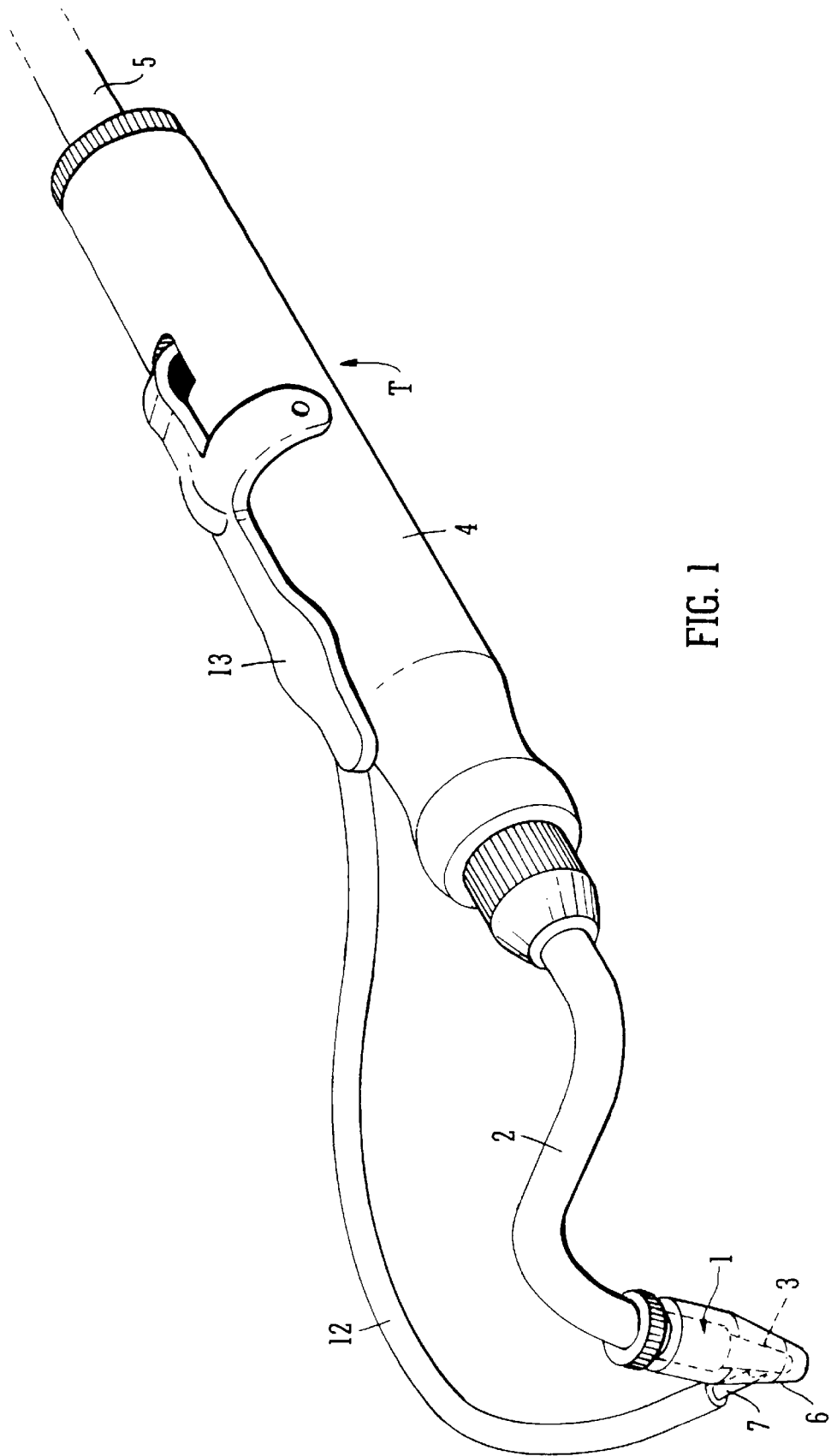
FIG. 1 is a perspective view of one tool of the invention.

As shown in FIG. 1, the front or head portion of the dental cutting tool T comprises an air/abrasive nozzle 1 which is secured to the front end of a stainless steel gas/abrasive delivery tube 2. The nozzle has a tapered front portion 3, and the outlet is of relatively small diameter. Preferably, the front portion 3 is made of tungsten or the like. The air/abrasive delivery tube 2 is in the form of a swan neck to enable access of the cutting jet to the rear surfaces of a patient's teeth. The tube 2 is connected to a tool body 4 having an inlet 5 which, in turn, is connected to a reservoir of abrasive and of pressurised air, not shown. When air is passed along the body 4 and the tube 2 to the front portion 3 a stream S of flow gas emerges at a preselected gas pressure. (The stream may be made of gas or of gas and abrasive particles.)

Figure 2:
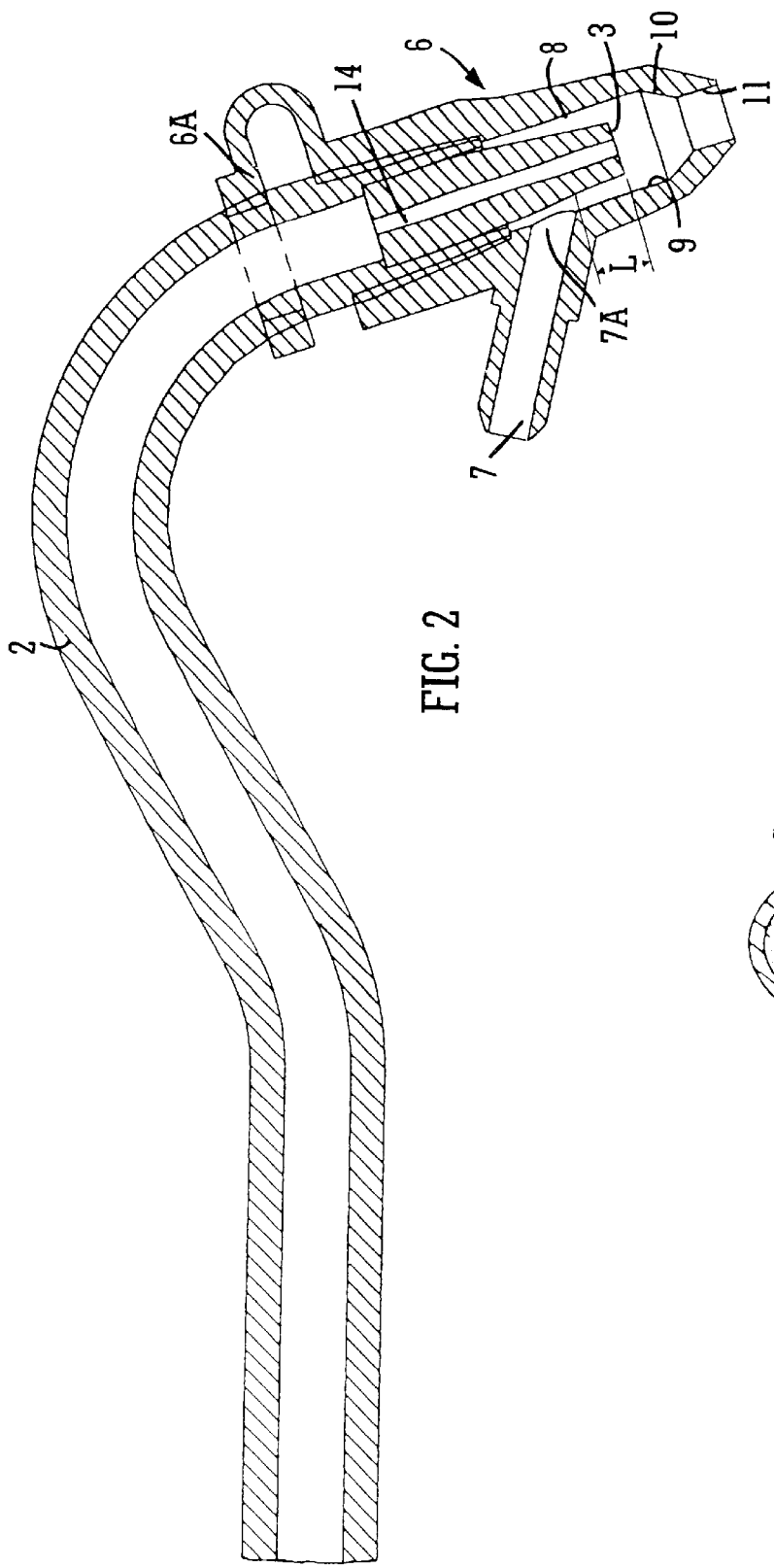
FIG. 2 is a longitudinal section of the front portion of the tool of FIG. 1.
Figure 4:
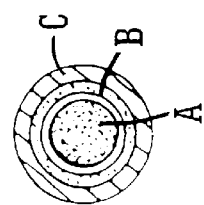
FIG. 4 is a transverse sectional view taken on line IV—IV on FIG. 3.
Figure 3:
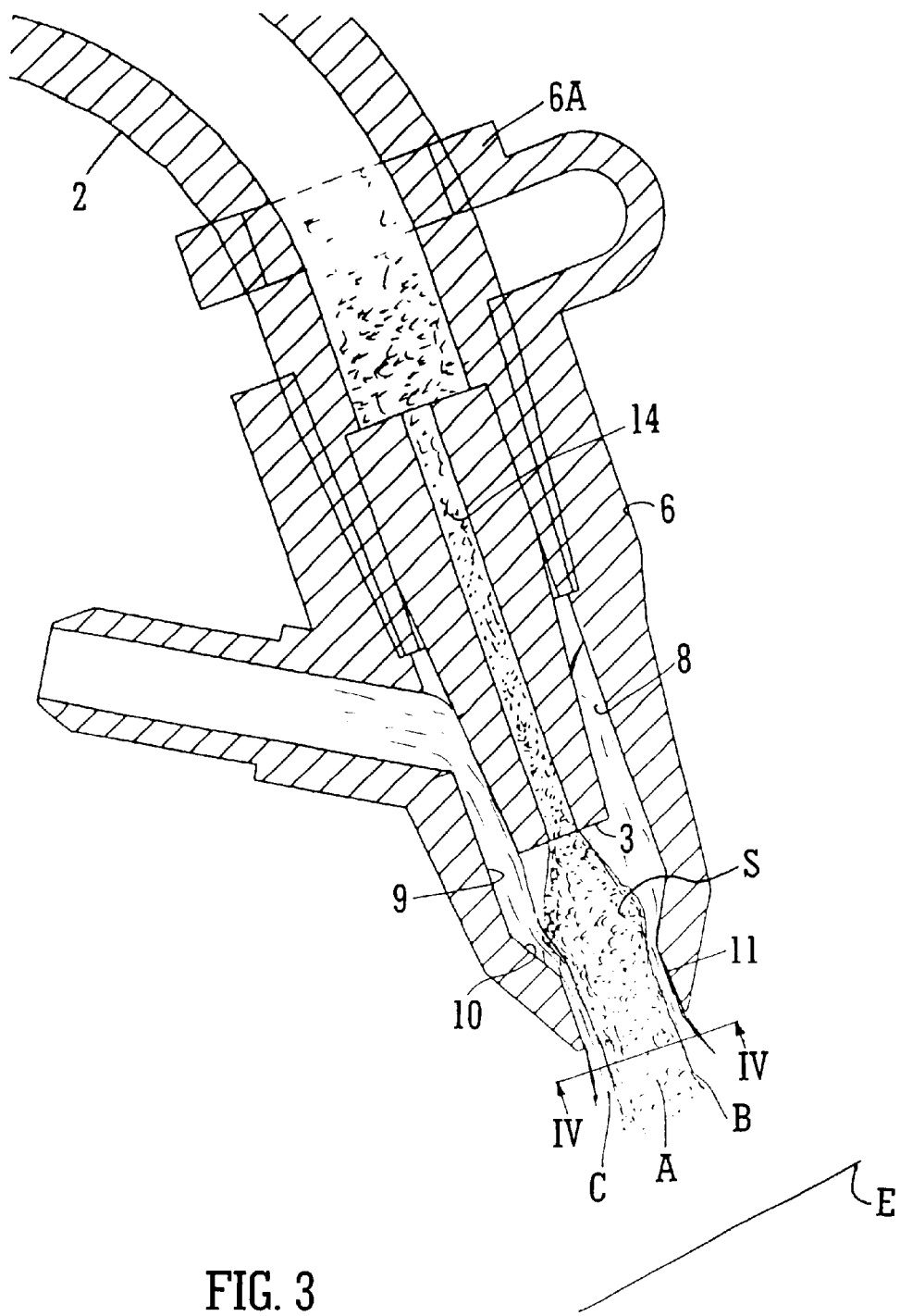
FIG. 3 is an enlarged sectional view of the cap member at the front of the dental tool showing stylistically the flow of abrasive media and water.

A cap 6 is mounted over the nozzle 1 and is held to the nozzle by a circular clip 6A which fits over the tube 2. The nozzle has a central delivery passageway 14. The cap is made of translucent or transparent plastics and has an internal tapered shape as shown in FIG. 2 and in greater detail in FIG. 3. The cap 6 has a branch 7 forming a water inlet 7A which enters its main bore 8 rearwardly of the outlet of nozzle front portion 3. The bore 8 has a main parallel sided portion 9 leading to a forward tapered portion 10 leading to a leading parallel sided portion 11. The diameter of the parallel sided portion 11 is greater than that of the passageway 14 so that the emergent gas stream will tend to flare outwardly. The portion 11 is generally in axial alignment with the passageway 14. The position of the inlet 7A is selected so that suction is generated by the Venturi effect of the flowing gas stream on the unpressurised water, i.e. there is a longitudinal distance L rearwardly of the outlet of the nozzle 1 and the inlet 7. The inlet 7 is connected by a pipe 12 to a reservoir, not shown, containing unpressurised water or other liquid. The pipe contains a check valve, not shown, to prevent backflow. It has been discovered according to the invention that the water flows into the bore 8 to form an annular curtain about the front portion 3 and is drawn by the Venturi effect in the bore 8 of the cap 6 in advance of the portion 3 to form an outer flaring cylindrical curtain C of water adjacent the wall of the bore 8 and a somewhat similar cylindrical zone B of water and abrasive is formed at the interface with air/abrasive jet A (see FIGS. 3 and 4). A cutting zone is defined by the boundary of zone at its interception with tooth surface E.

A lever 13 is pivotally mounted on the body 1 and incorporates a pinch valve, not shown. The pipe 12 passes through the valve, so that the dentist can use finger control on the tool to control the flow of water.

In use, the water is drawn into nozzle 1 by the Venturi action of the gas stream or jet and flows around the forward portion 3 of nozzle and forms the curtain which captures the abrasive particles and prevents them from being dispersed in the patient's mouth and airways. The pressure of the stream controls the volume of the liquid drawn to form the curtain. The pressure of the stream draws the liquid by the laminar flow of the outside surface of the stream of gas abrasive. The liquid is introduced such that it creates a complete curtain of liquid around the main jet drawn forward by Venturi effect without any tendency to affect its velocity. If the supply of unpressurised water is stopped, the gas stream emerging from the passageway 14 will tend to flare out to contact the tapered wall 10. The evidence for this is the abrasion of those surfaces. The water drawn in forming the curtain protects that wall and there is no evidence of such abrasion even though the abrasive particles are flared out towards that tapered wall.

The tip of cap 6 is held about two to three millimeters from tooth surface E and the supply of water can be controlled by adjusting thumb pressure on a control lever 13. The velocity and volume of the water stream automatically varies in accordance with the velocity of the air/abrasive stream. The water irrigates the abrasive in the cutting region so dramatically improving cutting performance. The slurry of abrasive particles in water formed at the tooth surface is easily removed by conventional aspiration equipment.

In a variant the water could be supplied to inlet 7 from a disposable one-use pack. A dentally acceptable sterilising agent or other additive useful in dentistry could be added to the water, e.g. a drug or anaesthetic or flavour or surfactant. The abrasive particles can, for example, be of silica or sodium bicarbonate depending on the degree of abrasion required. In particular, relatively soft particulate material could be used in polishing applications.

The advantages of the invention are that a total curtain of liquid can surround the jet or stream of gas and abrasive to contain the gas and abrasive totally and continuously. The curtain of liquid is developed in such a way as to be totally intimate with and surrounding the gas powder stream such that they do not mix until they impact with the surface being treated.

The liquid and the gas powder stream are configured such that the surrounding liquid curtain is largely self-adjusting i.e. if the pressure of the gas powder stream is increased or decreased, the strength and volume of the liquid curtain is increased or decreased. The curtain limits the divergence of the jet of gas and powder as it leaves the tip of the instrument keeping the gas powder stream concentrated and focused on the surface to be worked on which can increase the cutting effectiveness by up to almost 100%. The improvement in performance is a result of the combination of the dry stream and the irrigation effect of the liquid shield. The slurry of liquid and debris can be removed simply by conventional evacuation techniques that the dentist uses when using a conventional rotary cutting instrument with its coolant.

The tool is compact and shaped such that it is pointed towards its working end so as to give good visibility of the cutting area externally of the tip during the cutting procedure. The tool can be disposable after every treatment at minimum cost.

The tip of the instrument can be used wet or dry by the simple expedient of a valve controlling the supply of liquid from the reservoir.

Figure 5:
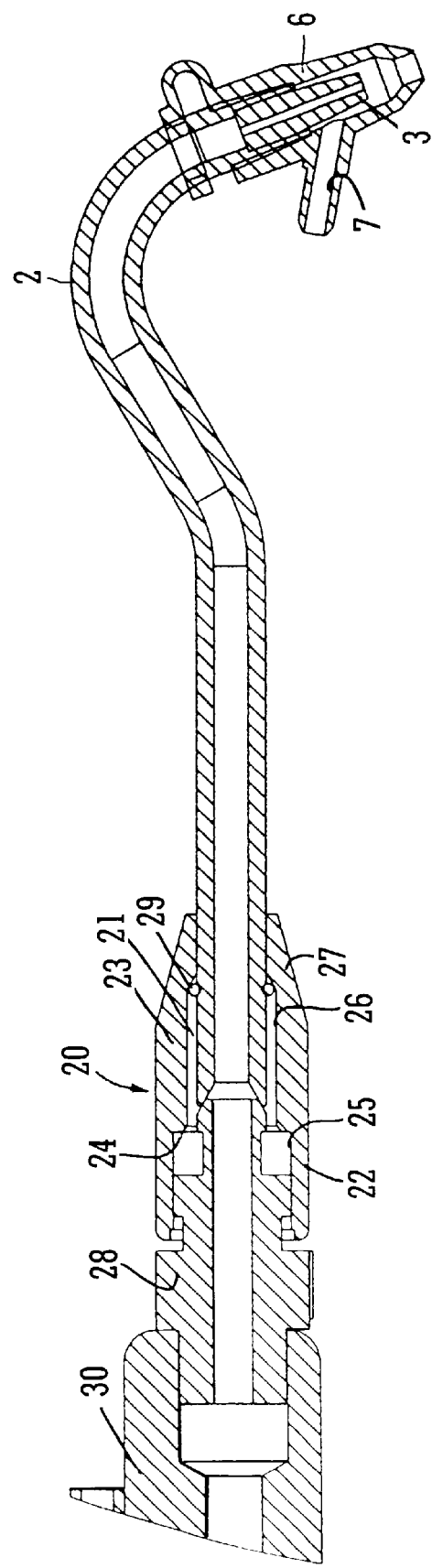
FIG. 5 is a longitudinal section of an assembly at the leading end of a dental tool.

As shown in FIG. 5, the delivery tube 2 of the dental tool body consists of a connector 20 having a bore 21 divided in two portions 22, 23, by a shoulder 24. The distal end portion 22 has an internally threaded wall 25 which receives the externally threaded portion of a nipple junction 28 connected to the adjacent part 30 of the tool body whereby the abrasive particles are kept away from the threads. The bore portion 23 has a short tapering portion 26, leading to a parallel sided portion 27 dimensioned to receive the distal end of the nozzle tube 2. A circlip 29 is received in the tapered portion 26; the outer surface of the nozzle tube has a slight groove to receive the circlip. As a result, the nozzle tube can rotate within the connector but not be moved axially. Because the tube 2 has a swan neck it can be rotated for the dentist to gain access to the rear of a tooth without the need to remove the instrument from the patient's mouth.

The invention is not limited to the embodiment shown. The tube need not be a swan neck. The inclined portion of the passageway forward of the nozzle outlet will be at an inclination appropriate to the nozzle diameter, the pressure of the gas stream and like factors. A further valve can be incorporated to enable the instrument to supply an air stream only to the powder enabling drying and purging of the area with clean air. In addition, a valve may be present in the water pipeline to ensure that when the lever 9 is shut, water is removed from the nozzle and cap volume to avoid wetting of any residual powder.

What is claimed is:

1. A dental tool arranged to be coupled to a supply of unpressurized liquid, said tool comprising a body having a nozzle for providing a stream of pressurized gas containing abrasive media towards a tooth surface, said nozzle having an outlet and a bore, a cap member extending forwardly of the outlet end of the nozzle, said cap member having a bore in generally axial alignment with said bore of said nozzle, said bore of said cap member having a wall, said cap member having a liquid supply pipe opening into said bore of said cap member rearwardly of said nozzle outlet to draw the unpressurized liquid into said bore, said wall of said bore of said cap member forwardly of said nozzle being shaped so that liquid emerging from said cap member is caused by the gas stream to form a wall of liquid about the gas stream moving towards the tooth surface, which wall of liquid protects said wall of said bore of said cap member from abrasion by the abrasive media.

2. A tool according to claim 1, wherein said cap member is disposable.

3. A tool according to claim 1, wherein said cap member is made of a plastics.

4. A tool according to claims 1, 2 or 3, additionally comprising the supply of unpressurized liquid, and wherein said supply of unpressurized liquid is in the form of a disposable single-use pack.

5. A tool according to claims 1, 2 or 3, additionally comprising the supply of unpressurized liquid, and wherein said supply of unpressurized liquid is in the form of a disposable single-use pack and wherein said single-use pack is integral with said cap.

6. A tool according to claim 1, additionally comprising the supply of unpressurized liquid and manually operated external means for controlling said supply of unpressurized liquid.

7. A tool according to claim 1, additionally comprising the supply of unpressurized liquid and wherein said supply of unpressurized liquid contains a sterilizing agent, anaesthetic, flavoring agent or surfactant.

8. A dental tool arranged to be coupled to a supply of unpressurized liquid, said tool comprising a body having a nozzle having an outlet end and a bore for providing a stream of pressurized gas containing abrasive media towards a tooth surface, wherein said stream of pressurized gas draws the unpressurized liquid into said bore to form a wall of liquid about the gas stream, and a cap member, said cap member being mounted on said outlet end of said nozzle and extending forwardly thereof, said cap member having a bore in general axial alignment with said bore of said nozzle, said bore of said cap member having a wall shaped to allow the gas/abrasive media stream to flare outwardly, the unpressurized liquid entering said bore of said cap member at a location to draw the liquid into said bore of the cap member by a venturi effect, the wall of liquid acting to protect said wall of said bore of said cap member from abrasion by the abrasive media.

9. A dental tool arranged to be coupled to a supply of unpressurized liquid, said tool comprising a body having a nozzle having an outlet end for providing a stream of pressurized gas containing abrasive media towards a tooth surface, a cap member extending forwardly of said outlet end of said nozzle, said cap member having a bore in generally axial alignment with said bore of said nozzle, said bore of said cap member having a wall, said cap member having a liquid supply pipe opening into said bore of the cap rearwardly of said nozzle outlet end to draw the unpressurized liquid into said bore of said cap member, the distance from said liquid supply pipe opening to said nozzle outlet end being selected to generate a venturi effect on the unpressurized liquid and whereby the pressure of the pressurized gas controls the volume of unpressurized liquid drawn into said nozzle, said wall of said bore of said cap member forwardly of said nozzle being shaped so that liquid emerging from said outlet end is caused by the gas stream to form a wall of liquid about the gas stream moving towards the tooth surface, which wall of liquid protects said wall of said bore of said cap member from abrasion by the abrasive media.

10. A method of treating a tooth, the method comprising drawing a stream of pressurized gas towards the tooth surface, the gas containing abrasive media, said method comprising:

(a) using a nozzle to deliver said gas stream and abrasive particles to the tooth surface;

(b) using a cap member in conjunction with said nozzle, said cap member having a bore defined by a wall having shaped surfaces; and (c) drawing an unpressurized liquid to join the gas stream wherein the unpressurized liquid is passed with the pressurized gas along said shaped surfaces of said bore of said cap member and is shaped by a venturi effect to form a wall about said gas stream before said gas stream reaches the tooth surface, whereupon said liquid protects said wall of said bore from abrasion by the abrasive media.

* * * * *